(12) United States Patent
Lin et al.

(10) Patent No.: US 12,159,691 B2
(45) Date of Patent: Dec. 3, 2024

(54) METHOD FOR ANALYSIS AND DETERMINATION OF HEAVY METAL OCCURRENCE KEY MINERAL PHASES IN INDUSTRIAL SOLID WASTE

(71) Applicant: Central South University, Changsha (CN)

(72) Inventors: Zhang Lin, Changsha (CN); Le Lin, Changsha (CN); Yanjie Liang, Changsha (CN); Xueming Liu, Changsha (CN); Yong Ke, Changsha (CN); Xu Yan, Changsha (CN); Chen Tian, Changsha (CN); Zhangbin Liu, Changsha (CN)

(73) Assignee: Central South University, Changsha (CN)

( * ) Notice: Subject to any disclaimer, the term of this patent is extended or adjusted under 35 U.S.C. 154(b) by 0 days.

(21) Appl. No.: 17/990,501

(22) Filed: Nov. 18, 2022

(65) Prior Publication Data

US 2023/0117820 A1 Apr. 20, 2023

Related U.S. Application Data

(63) Continuation of application No. PCT/CN2022/087877, filed on Apr. 20, 2022.

(30) Foreign Application Priority Data

Aug. 19, 2021 (CN) .......................... 202110952760.2

(51) Int. Cl.
*G16C 20/20* (2019.01)
*G01N 23/2055* (2018.01)

(52) U.S. Cl.
CPC ......... *G16C 20/20* (2019.02); *G01N 23/2055* (2013.01); *G01N 2223/0566* (2013.01); *G01N 2223/637* (2013.01); *G01N 2223/652* (2013.01)

(58) Field of Classification Search
CPC ........ G16C 20/20; G16C 20/10; G16C 20/30; G01N 23/2055; G01N 2223/0566;
(Continued)

(56) References Cited

U.S. PATENT DOCUMENTS 4,629,785 A * 12/1986 McCaffery, III ......... C07K 1/20
530/859

FOREIGN PATENT DOCUMENTS

BR PI0802824 A2 3/2010
CN 101718721 A 6/2010
(Continued)

OTHER PUBLICATIONS

Zhou, Huihui, and et al. "Mineralogical and morphological factors affecting the separation of copper and arsenic in flash copper smelting slag flotation beneficiation process." Journal of Hazardous Materials 401 (Jan. 2021): 123293 (Year: 2021).*
(Continued)

*Primary Examiner* — Douglas Kay
(74) *Attorney, Agent, or Firm* — Nitin Kaushik

(57) ABSTRACT

The present invention provides a method for analysis and determination of the heavy metal occurrence key mineral phases in industrial solid waste, by performing N concentration gradients dissociation determination of the heavy metal solid waste to be tested under the same dissociation conditions, to give the dissociation degrees of the heavy metal elements to be tested at N different concentration gradients; the dissociated solid residues after dissociation being quantitatively analyzed for the mineral phase, to give
(Continued)

the relative content of each mineral phase in the M mineral phases of the heavy metal solid waste to be tested; then calculating to give the occurrence distribution proportion of the heavy metal elements in the mineral phase, which are accumulated from high to low; the occurrence key mineral phase whose cumulative occurrence proportion exceeds the preset cumulative threshold value is determined to be the key mineral phase of the heavy metal elements.

8 Claims, 2 Drawing Sheets

(58) Field of Classification Search
CPC ....... G01N 2223/637; G01N 2223/652; G01N 23/20; G01N 2223/605; G01N 21/3103; G01N 21/6404; G01N 21/73; G01N 27/626
See application file for complete search history.

(56) References Cited

FOREIGN PATENT DOCUMENTS

| | | | |
|---|---|---|---|
| CN | 107653380 A | 2/2018 | |
| CN | 109254023 A | 1/2019 | |
| CN | 111060417 A | 4/2020 | |
| CN | 111418080 A | 7/2020 | |
| CN | 111562353 A | 8/2020 | |
| CN | 111638244 A | 9/2020 | |
| CN | 111751513 A | 10/2020 | |
| CN | 114199978 * | 3/2022 | |
| DE | 69929211 T2 * | 9/2006 | ........... B09B 3/0041 |
| JP | 2014174123 A | 9/2014 | |
| WO | WO-2010022441 A1 * | 3/2010 | ............. B01D 11/04 |

OTHER PUBLICATIONS

Peter S. Hooda and et al, "Trace elements in soils", 2010 Blackwell Publishing Ltd. ISBN: 978-1-405-16037-7 (Year: 2010).*

Rodgers, Kiri J., and et al. "Enhanced characterisation for the management of industrial steel processing by products: potential of sequential chemical extraction." Environmental monitoring and assessment 191 (2019): 1-19 (Year: 2019).*

Boateng, Emmanuel. "Distribution of Co, Cu and Pb in different Particle-size fractions of Polluted Zambian Wetland Sediments using BCR Sequential Extraction Procedure." Ghent University (2015) (Year: 2015).*

Filgueiras, Ana V., and et al. "Chemical sequential extraction for metal partitioning in environmental solid samples." Journal of Environmental Monitoring 4, No. 6 (2002): 823-857 (Year: 2002).*

Malsiu, Avni, and et al. "Assessment of heavy metal concentrations with fractionation method in sediments and waters of the Badovci Lake (Kosovo)." Journal of Environmental and Public Health 2020 (2020) (Year: 2020).*

* cited by examiner

METHOD FOR ANALYSIS AND DETERMINATION OF HEAVY METAL OCCURRENCE KEY MINERAL PHASES IN INDUSTRIAL SOLID WASTE

CROSS-REFERENCE TO RELATED APPLICATIONS

The application claims priority to Chinese patent application No. 202110952760.2, filed on Aug. 19, 2021, the entire contents of which are incorporated herein by reference.

TECHNICAL FIELD

The present invention relates to the technical field of material detection and analysis, in particular to a method for analysis and determination of heavy metal occurrence key mineral phases in industrial solid waste.

BACKGROUND

Industrial solid waste is easy to cause various types of environmental pollution, among which the pollution caused by heavy metal industrial solid waste has the worst impact. Therefore, reasonable disposal of industrial solid waste containing heavy metals becomes particularly important.

In order to treat and dispose heavy metal industrial solid waste reasonably, the first thing is to systematically analyze the occurrence state of heavy metals in industrial solid waste. At present, Tessier five-step continuous extraction method and BCR three-step continuous extraction method are commonly used to determine the occurrence status in the field of environment. These two methods were first developed to explore the morphology of heavy metals in river sediments and soil, and were later applied to the related research of solid waste. However, due to the lack of standard reference materials for solid waste, the rationality of the spontaneous migration application of researchers has not been verified. Secondly, Tessier continuous extraction method divides heavy metals into five binding forms: ion exchange state, carbonate binding state, iron (manganese) oxide binding state, organic matter and sulfide binding state, and residue state, while BCR continuous extraction method divides heavy metals into acid extractable state, reducible state, oxidizable state and residue state. However, these two methods can only summarize the occurrence states of heavy metals into several categories with the same or similar chemical properties, without knowing the quantitative information of the occurrence of heavy metals in specific mineral phases, which is unable to meet the increasingly refined and customized design of industrial solid waste treatment and disposal schemes. In addition, due to the inherent defects of continuous extraction operation, each step can only be started after the completion of the previous step, and experimental period thereof is relatively long.

Therefore, it is necessary to develop a new method for analysis and determination of the heavy metal occurrence key mineral phases in industrial solid waste, so as to accurately and reliably quantify the occurrence proportion of heavy metals in each mineral phase, and determine the heavy metal occurrence key mineral phases that affect the choice of treatment and disposal technology.

SUMMARY

The main purpose of the present invention is to provide a method for analysis and determination of the heavy metal occurrence key mineral phases in industrial solid waste, aiming to solve the technical problem that the characterization method of the heavy metal occurrence key mineral phases in industrial solid waste is complex and cannot be quantified in the prior art.

To achieve the above purpose, the present invention provides a method for analysis and determination of the heavy metal occurrence key mineral phases in industrial solid waste, including the following steps:

S1, the content of heavy metal elements in the heavy metal solid waste to be tested is determined, to give the content of p kinds of heavy metal elements to be determined in the heavy metal solid waste to be tested;

S2, n concentration gradients dissociation determination of the heavy metal solid waste to be tested are performed under the same dissociation conditions, to give the dissociation degrees of the heavy metal elements to be determined at n different concentration gradients $$Exp_{n \times p} = \begin{pmatrix} d_{11} & \cdots & d_{1p} \\ \vdots & d_{ij} & \vdots \\ d_{n1} & \cdots & d_{np} \end{pmatrix},$$

the $d_{ij}$ represents the dissociation degree of the heavy metal element j to be determined in the i-th concentration gradient dissociation determination, $d_{ij} \in (0,1)$, i=1, 2, 3 . . . , n, j=1, 2, . . . , p;

S3, the dissociated solid residues after dissociation in step S2 is quantitatively analyzed for the mineral phase, to give the relative content $W_{ik}$ of each mineral phase in m mineral phases of the heavy metal solid waste to be tested, then according to the formula $$l_{ik} = \frac{m_o W_{ok} - m_i W_{ik}}{m_o W_{ok}},$$

the dissociation degrees of each mineral phase $$L_{n \times m} = \begin{pmatrix} 1_{11} & \cdots & 1_{1m} \\ \vdots & 1_{ik} & \vdots \\ 1_{n1} & \cdots & 1_{nm} \end{pmatrix}$$

is calculated, wherein k=1, 2, 3, . . . , m, $l_{ik}$ represents the dissociation degree of the mineral phase k in the i-th concentration gradient dissociation determination, $W_{ok}$ is the mass fraction of the mineral phase k in the heavy metal solid waste to be tested under the initial conditions, $m_0$ is the initial sample mass of the heavy metal solid waste to be tested, $m_i$ is the mass of the dissociated solid residue after the i-th concentration gradient determination, and $W_{ik}$ is the mass fraction of the mineral phase k in the dissociated solid residue after the i-th concentration gradient determination;

S4, according to the formula $L_{n \times m} \times R_{m \times p} = Exp_{n \times p}$, the occurrence distribution proportion of the heavy metal element in the mineral phase $$R_{m \times p} = \begin{pmatrix} r_{11} & \cdots & r_{1p} \\ \vdots & r_{kj} & \vdots \\ r_{m1} & \cdots & r_{mp} \end{pmatrix}, r_{kj} \in (0, 1)$$

is solved;

S5, the occurrence distribution proportions of the heavy metal element j in the mineral phase are accumulated from high to low, and the mineral phase whose cumulative occurrence proportion exceeds the preset cumulative threshold value is determined to be the occurrence key mineral phase of the heavy metal element j.

Further, the calculating formula of the $d_{ij}$ includes $$d_{ij} = \frac{c_{ij}V_{ij}}{\omega_{0j}m_0}, \omega_{0j}$$

is the mass fraction of the heavy metal element j in the heavy metal solid waste to be tested under the initial conditions, $c_{ij}$ is the concentration of the heavy metal element j in the dissociated solution after the i-th concentration gradient determination, and $V_{ij}$ is the volume of the dissociated solution after the i-th concentration gradient determination.

Further, before step S2, it also includes pre-cleaning the heavy metal solid waste to be tested; wherein the calculating formula of the $\omega_{0j}$ is $$\omega_{0j} = \frac{\omega'_j m_a - c'_j V}{m_b},$$

wherein $\omega'_j$ is the mass fraction of the heavy metal element j in the heavy metal solid waste to be tested without pre-cleaning, $m_a$ is the mass of the heavy metal solid waste to be tested without pre-cleaning, $m_b$ is the mass of the heavy metal solid waste to be tested after pre-cleaning, $c'_j$ is the concentration of the heavy metal element j in the cleaning solution of the heavy metal solid waste to be tested after pre-cleaning, V is the volume of the cleaning solution of the heavy metal solid waste to be tested after pre-cleaning.

Further, the pre-cleaning steps include: 0.1 mol/L ammonium acetate solution with pH=7.0 is used as the pre-cleaning reagent, which is mixed with the heavy metal solid waste to be tested at a liquid-solid ratio of 10 L: 1 kg, then oscillated horizontally for 1-2 h at 15-35° C., the obtained solution is centrifuged at 6000 rpm-10000 rpm for 3-10 min to give the cleaning solution and the heavy metal solid waste to be tested after pre-cleaning: the content of the heavy metal elements in the cleaning solution is measured, and the heavy metal solid waste to be tested after pre-cleaning is quantitatively analyzed for the mineral phase.

Further, before the step S1, it also includes the step of pre-treatment of the heavy metal solid waste to be tested; the sample of the heavy metal solid waste to be tested is air-dried at 60-105° C. and ground to a sample powder with a size below 200 meshes.

Further, the steps of n concentration gradients determination under the same dissociation conditions include: at the same time and under the same outer field effect, the solid waste is nonspecifically dissociated in acid solutions with n concentration gradients, and the content of heavy metal element in the dissociated solution after dissociation is measured; wherein the acid solution is a mixed acid with nitric acid: hydrochloric acid in mol ratio of 1:3; the dissociation liquid-solid ratio is 8-12 L:1 kg, the temperature is 15-35° C., and the dissociation time is 1-2 h; and the outer field effect includes ultrasonic waves with an ultrasonic frequency of 20 kHz-40 KHz, and a power of 200-500 W.

Further, the number of n is equal to the number of mineral phases m of the heavy metal solid waste to be tested, wherein the hydrogen ion concentration range of the acid solution in the n concentration gradients dissociation determination is 0-12 mol/L.

Further, the steps of quantitative analysis of the mineral phase include: an X-ray diffraction pattern is obtained through X-ray diffraction analysis, and the relative contents of all mineral phases in the dissociated solid residue are determined based on the marked Rietveld full spectrum fitting and refining method, wherein the mineral phase not included in the dissociated solid residue is selected as the internal standard substance, which includes alumina or zinc oxide.

Further, the preset cumulative threshold value is 80%-95%.

Further, the method for measuring the content of heavy metal elements is one or any combination of inductively coupled plasma emission spectroscopy, atomic absorption spectroscopy, inductively coupled plasma mass spectrometry, the atomic fluorescence spectroscopy.

In the present invention, by multi-dimensional information obtained from the coupling experimental analysis and instrument characterization, N concentration gradients dissociation determination of the heavy metal solid waste to be tested are performed under the same dissociation conditions, to give the dissociation degrees of the heavy metal elements to be tested at N different concentration gradients: the dissociated solid residue after dissociation is quantitatively analyzed for the mineral phase, to give the relative content of each mineral phase in the M mineral phases of the heavy metal solid waste to be tested; then it is solved to give the occurrence distribution proportions of the heavy metal element in the mineral phase, which are accumulated from high to low: the occurrence key mineral phase whose cumulative occurrence proportion exceeds the preset cumulative threshold value is determined to be the occurrence key mineral phase of the heavy metal element. It provides a simple, fast, efficient and accurate method for analysis and determination of the heavy metal occurrence key mineral phases in industrial solid waste, realizes the accurate analysis of the occurrence status of heavy metals in industrial solid waste, and provides refined technical support for the selection of industrial solid waste treatment and disposal technologies.

BRIEF DESCRIPTION OF DRAWINGS

In order to more clearly state the technical solution in the embodiment of the invention or in the art, the attached drawings required to be used in the description of the embodiment or prior art are briefly described below. It is obvious that the attached drawings described below are only some embodiments of the invention and that other drawings may be available to ordinary technicians in the field on the basis of these structures without creative effort.

The purpose, functional characteristics and advantages of the invention will be further explained by referring to the attached drawing in combination with the embodiment.

DETAILED DESCRIPTION OF THE EMBODIMENTS

The technical solution in the embodiment of the invention will be clearly and completely described below in combination with the attached drawings in the embodiment of the invention. Obviously, the described embodiments are only a part of the embodiments of the invention, but not all embodiments. Based on the embodiment of the invention, all other embodiments obtained by ordinary technicians in the field without creative effort fall within the protection scope of the invention.

It needs to be stated that all directional indications in the embodiment of the invention (such as up, down . . . ) are only used to explain the relative position relationship and movement of each component under a specific attitude (as shown in the attached picture). If the specific attitude is changed, the directional indication will be changed accordingly.

In addition, in the present invention, descriptions referring to "first", "second", etc., are used only for descriptive purposes and are not to be understood as indicating or implying their relative importance or implicitly indicating the number of technical features indicated. Thus, a characteristic defined as "first" or "second" may explicitly or implicitly include at least one of these characteristics.

Moreover, the technical solutions among the various embodiments of the invention can be combined with each other, but it must be based on the situation that ordinary technical personnel in the art can realize. When the combination of technical solutions contradicts each other or cannot be realized, it should be considered that the combination of such technical solutions does not exist, nor within the protection scope claimed by the invention.

Figure 1:
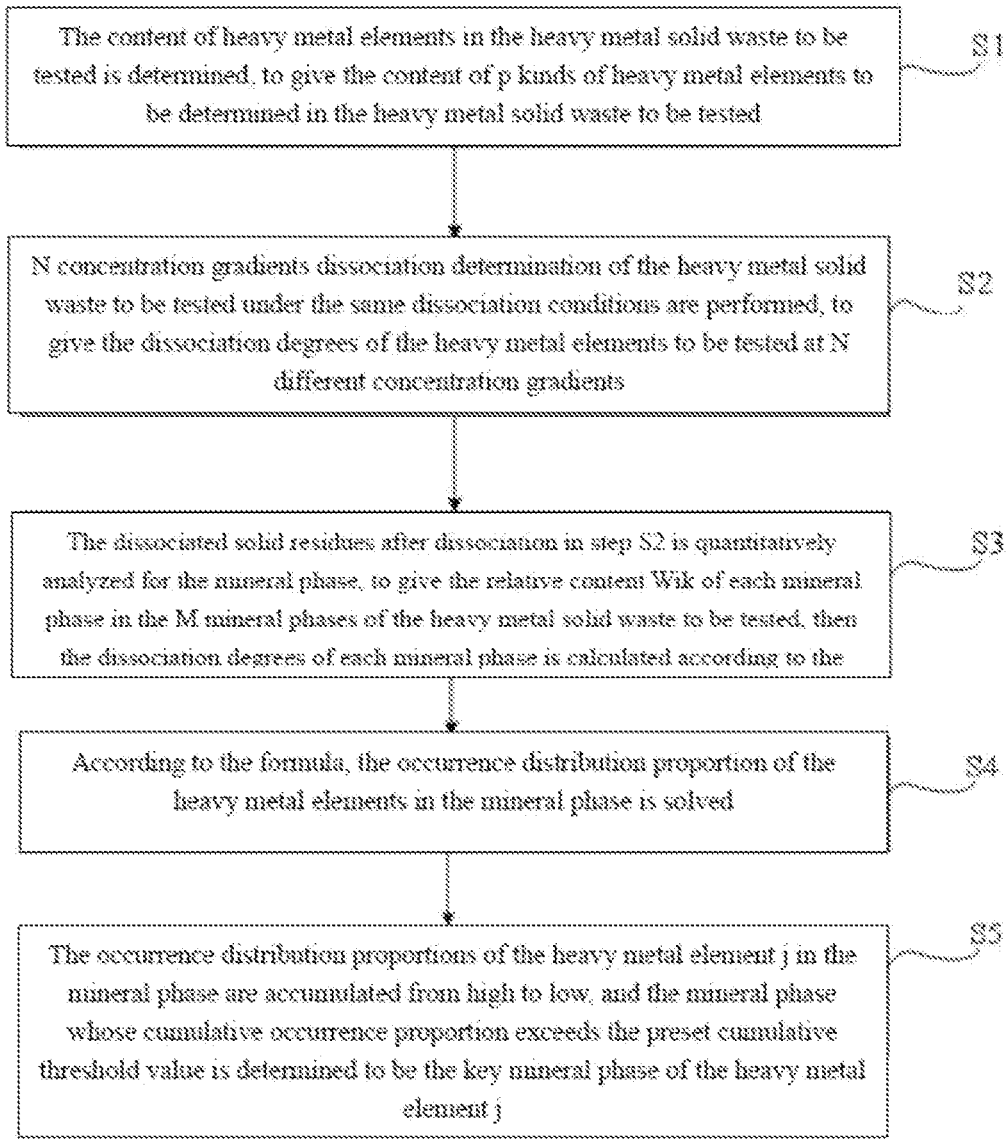
FIG. 1 is a flow chart of the method for analysis and determination of the heavy metal occurrence key mineral phases in industrial solid waste of the present invention.
Figure 2:
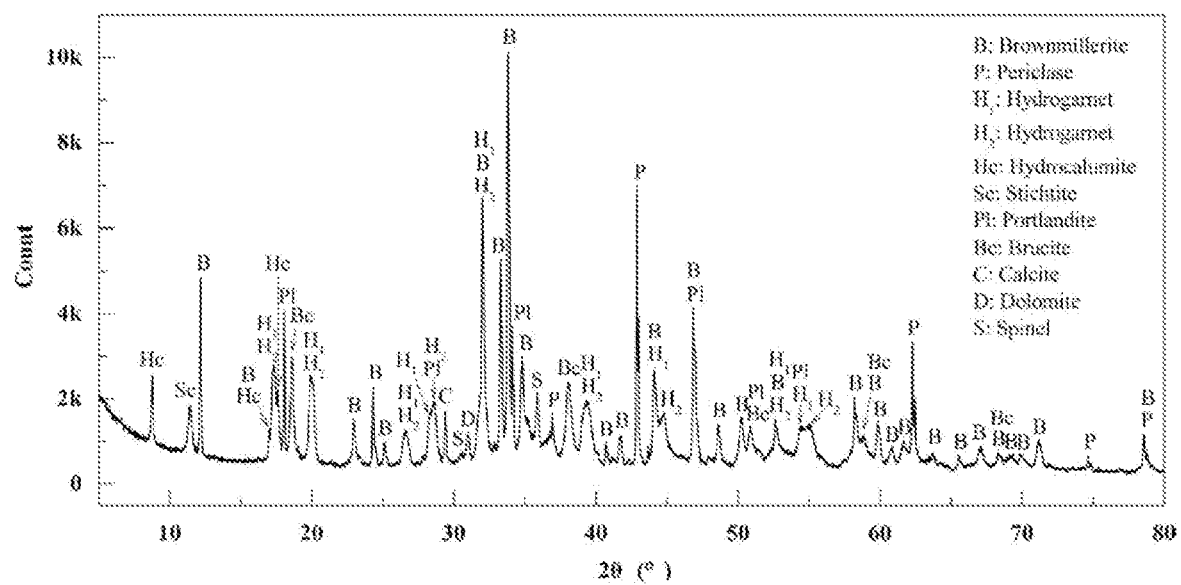
FIG. 2 shows the X-ray diffraction analysis pattern of chromium slag in an example.

Refer to FIG. 1, it is a method for analysis and determination of the heavy metal occurrence key mineral phases in industrial solid waste in a specific embodiment of the present invention, including the following steps:

S1, the content of heavy metal elements in the heavy metal solid waste to be tested is determined, to give the content of p kinds of heavy metal elements to be determined in the heavy metal solid waste to be tested;

Specifically, the content of heavy metal elements can be determined by qualitative method before quantitative method. The qualitative method can be X-ray fluorescence spectrum, and the quantitative method can be one or any combination of inductively coupled plasma emission spectrum, atomic absorption spectrum and laser-induced breakdown spectrum.

Further, before the step S1, it also includes the step of pre-treatment of the heavy metal solid waste to be tested; the sample of the heavy metal solid waste to be tested is air-dried at 60-105° C. and ground to a sample powder with a size below 200 meshes, then dried to constant weight.

S2, n concentration gradients dissociation determination of the heavy metal solid waste to be tested are performed under the same dissociation conditions, to give the dissociation degrees of the heavy metal element to be determined at n different concentration gradients $$\text{Exp}_{n \times p} = \begin{pmatrix} d_{11} & \cdots & d_{1p} \\ \vdots & d_{ij} & \vdots \\ d_{n1} & \cdots & d_{np} \end{pmatrix},$$

the $d_{ij}$ represents the dissociation degree of the heavy metal element j to be determined in the i-th concentration gradient dissociation determination, $d_{ij} \in (0,1)$, i=1, 2, 3, . . . , n, j=1, 2, . . . , p;

Specifically, the steps of n concentration gradients dissociation determination under the same dissociation conditions include: at the same time and under the same outer field effect, the solid waste is nonspecifically dissociated in acid solutions with n concentration gradients, and the content of the heavy metal element in the dissociated solution after dissociation is measured; wherein the acid solution is a mixed acid with nitric acid: hydrochloric acid in mol ratio of 1:3; the dissociation liquid-solid ratio is 8-12:1 (L/kg), the temperature is 15-35° C., and the dissociation time is 1-2 h; the outer field effect includes ultrasonic waves with an ultrasonic frequency of 20 KHz-40 KHz, and a power of 200-500 W. Wherein the method for measuring the content of heavy metal elements is one or any combination of inductively coupled plasma emission spectroscopy, atomic absorption spectroscopy, inductively coupled plasma mass spectrometry, the atomic fluorescence spectroscopy.

Further, the calculating formula of the $d_{ij}$ includes $$d_{ij} = \frac{c_{ij} V_{ij}}{\omega_{0j} m_0}, \omega_{0j}$$

is the mass fraction of the heavy metal element j in the heavy metal solid waste to be tested under the initial conditions, $c_{ij}$ is the concentration of the heavy metal element j in the dissociated solution after the i-th concentration gradient determination, and $V_{ij}$ is the volume of the dissociated solution after the i-th concentration gradient determination.

Further, before step S2, it also includes pre-cleaning the heavy metal solid waste to be tested; wherein the calculating formula of the $\omega_{0j}$ is $$\omega_{0j} = \frac{\omega'_j m_a - c'_j V}{m_b},$$

wherein $\omega'_j$ is the mass fraction of the heavy metal element j in the heavy metal solid waste to be tested without pre-cleaning, $m_a$ is the mass of the heavy metal solid waste to be tested without pre-cleaning, $m_b$ is the mass of the heavy metal solid waste to be tested after pre-cleaning, $c'_j$ is the concentration of the heavy metal element j in the cleaning solution of the heavy metal solid waste to be tested after pre-cleaning, V is the volume of the cleaning solution of the heavy metal solid waste to be tested after pre-cleaning.

Further, the pre-cleaning steps include: 0.1 mol/L Ammonium acetate solution with pH=7.0 is used as a pre-cleaning reagent, which is mixed with the heavy metal solid waste to be tested at a liquid-solid ratio of 10:1 (L/kg), then oscillated horizontally for 1-2 h at 15-35° C., the obtained solution is centrifuged at 6000 rpm-10000 rpm for 3-10 min to give the cleaning solution and the heavy metal solid waste to be tested after pre-cleaning: the content of the heavy metal element in the cleaning solution is measured, and the heavy metal solid waste to be tested after pre-cleaning is quantitatively analyzed for the mineral phase. Wherein the method for measuring the content of heavy metal elements is one or any combination of inductively coupled plasma emission spectroscopy, atomic absorption spectroscopy, inductively coupled plasma mass spectrometry, the atomic fluorescence spectroscopy: the steps of quantitative analysis of the mineral phase include: an X-ray diffraction pattern is obtained through X-ray diffraction analysis, and the relative content of all mineral phases in the dissociated solid residue is determined based on the marked Rietveld full spectrum fitting and refining method, wherein the mineral phase not included in the dissociated solid residue is selected as the internal standard substance, which includes alumina or zinc oxide.

S3, the dissociated solid residues after dissociation in step S2 is quantitatively analyzed for the mineral phase, to give the relative content $W_{ik}$ of each mineral phase in m mineral phases of the heavy metal solid waste to be tested, then according to the formula $$I_{ik} = \frac{m_o W_{ok} - m_i W_{ik}}{m_o W_{ok}},$$

the dissociation degree of each mineral phase $$L_{n \times m} = \begin{pmatrix} l_{11} & \cdots & l_{1m} \\ \vdots & l_{ik} & \vdots \\ l_{n1} & \cdots & l_{nm} \end{pmatrix}$$

is calculated, wherein k=1, 2, 3, . . . , m, $l_{ik}$ represents the dissociation degree of the mineral phase k in the i-th concentration gradient dissociation determination, $W_{0k}$ is the mass fraction of the mineral phase k in the heavy metal solid waste to be tested under the initial conditions, $m_0$ is the initial sample mass of the heavy metal solid waste to be tested, $m_i$ is the mass of the dissociated solid residue after the i-th concentration gradient determination, and $W_{ik}$ is the mass fraction of the mineral phase k in the dissociated solid residue after the i-th concentration gradient determination.

Specifically, the number of n is equal to the number of mineral phases m of the heavy metal solid waste to be tested, wherein the hydrogen ion concentration range of the acid solution in n concentration gradients dissociation determination is 0-12 mol/L.

Specifically, the steps of quantitative analysis of the mineral phase include: an X-ray diffraction pattern is obtained through X-ray diffraction analysis, and the relative content of all mineral phases in the dissociated solid residue is determined based on the marked Rietveld full spectrum fitting and refining method, wherein the mineral phase not included in the dissociated solid residue is selected as the internal standard substance, which includes alumina or zinc oxide.

S4, according to the formula $L_{n \times m} \times R_{m \times p} = Exp_{n \times p}$, the occurrence distribution proportion of the heavy metal element in the mineral phase $$R_{m \times p} = \begin{pmatrix} r_{11} & \cdots & r_{1p} \\ \vdots & r_{kj} & \vdots \\ r_{m1} & \cdots & r_{mp} \end{pmatrix}, r_{kj} \in (0, 1)$$

is calculated.

Specifically, the occurrence distribution proportion of the heavy metal element in the mineral phase can be represented as:

$$R_{m \times p} = \begin{pmatrix} r_{11} & \cdots & r_{1p} \\ \vdots & r_{kj} & \vdots \\ r_{m1} & \cdots & r_{mp} \end{pmatrix}, r_{kj} \in (0, 1)$$

wherein each column vector $r_j$ in R represents the occurrence distribution of the heavy metal element j in m mineral phases, reflecting the proportion of the heavy metal element j allocated to mineral phase k. Therefore, there is the following relation: $L_{n \times m} \times R_{m \times p} = Exp_{n \times p}$, R can be solved by the following formula: $R_{n \times m} = L^+_{n \times m} \times Exp_{n \times p}$, wherein $L^+$ is the generalized inverse matrix of L matrix.

S5, the occurrence distribution proportions of the heavy metal element j in the mineral phase are accumulated from high to low; and the mineral phase whose cumulative occurrence proportion exceeds the preset cumulative threshold value is determined to be the occurrence key mineral phase of the heavy metal element j.

Optionally, in a specific embodiment, the preset cumulative threshold is 80%-95%. Specifically, the determination of the heavy metal occurrence key mineral phases is aimed for different heavy metals. The specific ones can be: referring to the Pareto law, after arranging the occurrence distribution portions of the heavy metal element j in each mineral phase from high to low; it can be considered that the occurrence key mineral phases of the heavy metal element j in the solid waste sample are the first few mineral phases whose cumulative distribution portion is equal to or exceeds 80%.

EXAMPLES

The object of this example was chromium slag produced by a chromium salt enterprise in Yunnan, which is a typical industrial solid waste containing heavy metals. Chromium element thereof is the most important heavy metal element in pollution control project.

Pretreatment steps: according to the method of the invention, the solid waste was preferably divided by quartering to take an appropriate amount of original sample, crushed by a crusher until it completely passed through a 200-mesh screen, and then placed in an open beaker and dried in a blast oven at 105° C. for 6 hours to a constant weight.

Pre-cleaning steps: 15.0000±0.005 g of the solid waste were taken, pre-cleaned by using 0.1 mol/L ammonium acetate solution with pH=7.0, under a liquid-solid ratio of 10:1 (L/kg), and the mixture was oscillated horizontally for 1 h at 25° C. in a shaker. The obtained solution was centrifuged at 8000 rpm for 10 min, washed three times, and the supernatant was set to a volume of 250 ml, diluted to the concentration range suitable for ICP-AES detection, and the content of the heavy metal element was determined by ICP AES. The residual solid was placed in an open beaker and dried in a blast oven at 105° C. for 8 hours to a constant weight. The analytical balance was used to weigh the solid waste sample before and after pre-cleaning, accurate to four decimal places.

Concentration gradient dissociation determination: it is known for technical personnel in this field that the method of strong acid digestion combined with instrument characterization is generally used for the content analysis of heavy metal elements in original samples. In this example, the solid waste was digested preferably by using aqua regia-HF—HClO$_4$ mixed acid system at 250° C., the residual clarified solution was set to a preset volume, diluted to the concentration range suitable for ICP-AES detection, and the content of the heavy metal element was determined by ICP-AES.

1.0000±0.005 g of the pre-cleaned sample were taken, and used for performing a series of concentration gradient dissociation experiments simultaneously. Specifically, in order to facilitate the operation, a mixed acid solution with a mol ratio of 1:3 was first prepared, wherein the concentration of hydrochloric acid was 9 mol/L and the concentration of nitric acid was 3 mol/L. The desired concentration gradients were then prepared by dilution, as 0.01 mol/L, 0.05 mol/L, 0.1 mol/L, 0.2 mol/L, 0.5 mol/L, 1 mol/L, 2 mol/L, 4 mol/L, 6 mol/L, 8 mol/L, 10 mol/L, 12 mol/L, respectively.

The basic principle of concentration gradient design was to ensure that all kinds of mineral phase particles have the chance to be completely dissociated or almost completely dissociated, and to make the dissociation degree of the same mineral phase different under different concentration experimental conditions. The number of gradient experiments should be equal to the number of mineral phases, that is, N=M=12. For solid waste with strong stability, such as slag and tailings, the gradient design of "sparse low concentration, dense high concentration" can be adopted. For the solid waste with poor stability, such as chemically precipitated sludge and fly ash, the gradient design of "dense low concentration, sparse high concentration" can be adopted. If it cannot be determined, the gradient design used in this example shall be adopted.

The solid waste sample was dissociated at a liquid-solid ratio of 10:1 (L/kg) for 1 h under the condition of 30 KHz ultrasonic wave and 25° C. After dissociation, the solution was centrifuged at 8000 rmp for 10 min, and the residue was washed three times with 20 ml deionized water, which was combined with the supernatant to a volume of 100 ml, and the content of heavy metal element was measured by ICP-AES after dilution. The solid part was dried for 8 h to a constant weight and weighed.

According to the formula $$\omega_{0j} = \frac{\omega'_j m_a - c'_j V}{m_b},$$

the dissociation degree of the heavy metal element Cr in the sample after pre-cleaning can be calculated. The details were as follows:

Table 1 Dissociation degree of the heavy metal element Cr in the sample after pre-cleaning

| W'$_j$(mg/g) | m$_a$(g) | m$_b$(g) | C'$_j$(mg/L) | V(L) | W$_{0j}$ (mg/g) |
|---|---|---|---|---|---|
| 47.55 | 15.0020 | 14.8320 | 593.0 | 0.250 | 38.10 |

In step S4, the dissociation degree of the heavy metal element Cr in each concentration gradient experiment (d1-d12) could be calculated by the formula $$d_{ij} = \frac{c_{ij} V_{ij}}{\omega_{oj} m_0},$$

as follows:

Table 2 Dissociation degree of the heavy metal element Cr in concentration gradient experiments (d1-d12)

| d$_1$ | d$_2$ | d$_3$ | d$_4$ | d$_5$ | d$_6$ |
|---|---|---|---|---|---|
| 0.031 | 0.037 | 0.094 | 0.210 | 0.339 | 0.522 |

| d$_7$ | d$_8$ | d$_9$ | d$_{10}$ | d$_{11}$ | d$_{12}$ |
|---|---|---|---|---|---|
| 0.539 | 0.771 | 0.790 | 0.883 | 0.942 | 0.955 |

The dissociated solid residue after dissociation was quantitatively analyzed for mineral phase: the quantitative analysis method for mineral phase was X-ray diffraction analysis (XRD). Specifically, the relative content of all mineral phases (including amorphous) was determined by the marked Rietveld full-spectrum fitting refinement method. The internal standard material was selected as excellent grade pure $\alpha$-Al$_2$O$_3$ powder, with a mixing ratio of 10%. It was known for the technicians in this field that Rietveld full-spectrum fitting refinement needs to be based on XRD fine scanning, and different analysis software can achieve the refinement function. In this example, Bruker's X-ray diffractometer was selected, and used for finely scanning in the range of 5-80° with a step size of 0.01°, and a step time of 2.5 s, and the data result analysis software was TOPAS.

According to the formula $$I_{ik} = \frac{m_o W_{ok} - m_i W_{ik}}{m_o W_{ok}},$$

the dissociation degree of the mineral phase for each concentration gradient dissociation experiment can be calculated. The details were as follows:

Table 3. Dissociation degree of the mineral phase for each concentration gradient dissociation experiment

| mineral phase | concentration 1 | concentration 2 | concentration 3 | concentration 4 | concentration 5 | concentration 6 |
|---|---|---|---|---|---|---|
| amorphous | 0.0097 | 0.0181 | 0.1139 | 0.3088 | 0.5255 | 0.833 |
| MgO | 0.0817 | 0.082 | 0.0839 | 0.0876 | 0.0918 | 0.0977 |
| Ca$_2$Fe$_{1.28}$Al$_{0.72}$O$_5$ | 0.0648 | 0.0687 | 0.0901 | 0.1338 | 0.1823 | 0.2512 |
| Ca$_3$Al$_{1.54}$Fe$_{0.46}$(OH)$_{12}$ | 0.05 | 0.057 | 0.0956 | 0.1741 | 0.2614 | 0.3953 |
| Ca$_{0.5}$Mg$_{0.5}$CO$_3$ | 0.0793 | 0.0802 | 0.0848 | 0.0941 | 0.1046 | 0.1193 |
| Ca$_4$Fe$_2$(CrO$_4$)(OH)$_{12}$·8H$_2$O | 0.0825 | 0.0826 | 0.0836 | 0.0856 | 0.0878 | 0.0909 |
| Mg$_6$Cr$_2$(CO$_3$)(OH)$_{16}$·4H$_2$O | 0.0818 | 0.0821 | 0.0838 | 0.0873 | 0.0911 | 0.0966 |
| MgAl$_{0.8}$Fe$_{1.2}$O$_4$ | 0.0832 | 0.0832 | 0.0833 | 0.0936 | 0.0839 | 0.0844 |
| Ca$_3$Al$_{2.849}$H$_{9.6}$O$_{12}$ | 0.0826 | 0.0827 | 0.0836 | 0.0852 | 0.087 | 0.0896 |
| CaCO$_3$ | 0.0742 | 0.0762 | 0.0867 | 0.108 | 0.1318 | 0.1655 |
| Mg(OH)$_2$ | 0.082 | 0.0823 | 0.0838 | 0.0869 | 0.0904 | 0.0954 |
| Ca(OH)$_2$ | 0.0816 | 0.082 | 0.0839 | 0.0879 | 0.0923 | 0.0986 |

| mineral phase | concentration 7 | concentration 8 | concentration 9 | concentration 10 | concentration 11 | concentration 12 |
|---|---|---|---|---|---|---|
| amorphous | 0.8616 | 0.9852 | 0.947 | 0.9996 | 1 | 1 |
| MgO | 0.0982 | 0.1418 | 0.1594 | 0.5291 | 1 | 1 |
| Ca$_2$Fe$_{1.28}$Al$_{0.72}$O$_5$ | 0.2576 | 0.7663 | 0.9716 | 0.9919 | 1 | 1 |

-continued

| | | | | | | |
|---|---|---|---|---|---|---|
| $Ca_3Al_{1.54}Fe_{0.46}(OH)_{12}$ | 0.3968 | 0.9051 | 0.9501 | 1 | 1 | 1 |
| $Ca_{0.5}Mg_{0.5}CO_3$ | 0.1207 | 0.23 | 0.2741 | 0.9298 | 1 | 1 |
| $Ca_4Fe_2(CrO_4)(OH)_{12} \cdot 8H_2O$ | 0.0912 | 0.1141 | 0.1234 | 0.3182 | 0.6629 | 0.8487 |
| $Mg_6Cr_2(CO_3)(OH)16 \cdot 4H_2O$ | 0.0971 | 0.1374 | 0.1337 | 0.4955 | 1 | 1 |
| $MgAl_{0.8}Fe_{1.2}O_4$ | 0.0844 | 0.0877 | 0.089 | 0.1169 | 0.1661 | 0.1926 |
| $Ca_3Al_{2.849}H_{9.6}O_{12}$ | 0.0899 | 0.1091 | 0.1169 | 0.2798 | 0.5682 | 0.7237 |
| $CaCO_3$ | 0.1686 | 0.4175 | 0.518 | 0.9891 | 1 | 1 |
| $Mg(OH)_2$ | 0.0958 | 0.1324 | 0.1472 | 0.4572 | 1 | 1 |
| $Ca(OH)_2$ | 0.0992 | 0.1456 | 0.1644 | 0.5578 | 1 | 1 |

Calculation of the occurrence distribution proportion of heavy metal elements in mineral phases: according to the formula $L_{n \times m} \times R_{m \times p} = Exp_{n \times p}$, $R_{n \times m} = L^+_{n \times m} \times Exp_{n \times p}$ was solved, wherein $L^+$ was the generalized inverse matrix of L matrix.

Specifically, in matlab, the dissociation degree data of the mineral phase was written into variable L in the form of matrix, and the dissociation degree data of the heavy metal element was written into variable E in the form of matrix, and R matrix can be solved by R-pinv(L)*E. The results were shown in Table 4.

Table 4. Occurrence distribution proportions of the heavy metal element in mineral phases

| | r |
|---|---|
| amorphous | 0.4846 |
| MgO | 0.0093 |
| $Ca_2Fe_{1.28}Al_{0.72}O_5$ | 0.1085 |
| $Ca_3Al_{1.54}Fe_{0.46}(OH)_{12}$ | 0.1952 |
| $Ca_{0.5}Mg_{0.5}CO_3$ | 0.0233 |
| $Ca_4Fe_2(CrO_4)(OH)_{12} \cdot 8H_2O$ | 0.0049 |
| $Mg_6Cr_2(CO_3)(OH)_{16} \cdot 4H2O$ | 0.0086 |
| $MgAl_{0.8}Fe_{1.2}O_4$ | 0.0007 |
| $Ca_3Al_{2.849}H_{9.6}O_{12}$ | 0.0041 |
| $CaCO_3$ | 0.0531 |
| $Mg(OH)_2$ | 0.0078 |
| $Ca(OH)_2$ | 0.0099 |

According to the method for determination of the occurrence key mineral phases, after the occurrence distribution proportions were arranged from high to low, it can be seen that the cumulative occurrence distribution portion of the heavy metal element Cr in amorphous phase, hydrogarnet $(Ca_3Al_{1.54}Fe_{0.46}(OH)_{12})$, calcium ferrite $(Ca_2Fe_{1.28}Al_{0.72}O_5)$ and calcium carbonate $(CaCO_3)$ was 0.8414 (greater than 0.8), such that the amorphous phase, hydrogarnet $(Ca_3Al_{1.54}Fe_{0.46}(OH)_{12})$, calcium ferrite $(Ca_2Fe_{1.28}Al_{0.72}O_5)$ and calcium carbonate $(CaCO_3)$ can be considered as the occurrence key mineral phases of the heavy metal element Cr in the solid waste.

Among the above-mentioned technical solutions of the present invention, the above is only a preferred example of the present invention, and is not therefore limiting the scope of the present invention. All equivalent structural transformations made using the contents of the specification and drawings of the present invention under the technical concept of the present invention, or directly/indirectly used in other related technical fields are included in the patent protection scope of the present invention.

What is claimed is:

1. A method for analysis of an industrial solid waste for determination of key mineral phases of heavy metal occurrence in the industrial solid waste, comprising following steps:

S1, determining contents of heavy metal elements in a heavy metal solid waste to be tested (HMSWtbt);

S2, performing dissociation of HMSWtbt in acid solutions with n concentration gradients under a set of dissociation conditions, wherein a same set of dissociation conditions to be used during each dissociation experiment in the acid solutions with the n concentration gradients to determine a plurality of dissociation degrees of the heavy metal element to be determined at n different concentration gradients $$Exp_{n \times p} = \begin{pmatrix} d_{11} & \cdots & d_{1p} \\ \vdots & d_{ij} & \vdots \\ d_{m1} & \cdots & d_{np} \end{pmatrix},$$

wherein $d_{ij}$ represents a dissociation degree of a heavy metal element j to be determined in an i-th concentration gradient after dissociation, $d_{ij} \in (0, 1)$, i=1, 2, 3, . . . , n, j=1, 2, . . . , p;

S3, quantitatively analyzing mineral phases in a dissociated solid residue after dissociation in step S2, determining a relative content $W_{ik}$ of each mineral phase in m mineral phases of the HMSWtbt, and then calculating a dissociation degree of each mineral phase expressed as $$L_{n \times m} = \begin{pmatrix} l_{11} & \cdots & l_{1m} \\ \vdots & l_{ik} & \vdots \\ l_{n1} & \cdots & l_{nm} \end{pmatrix}$$

according to a formula $$l_{ik} = \frac{m_o W_{ok} - m_i W_{ik}}{m_o W_{ok}},$$

wherein k=1, 2, 3, . . . , m, $l_{ik}$ represents a dissociation degree of a mineral phase k after dissociation at the i-th concentration gradient, $W_{ok}$ is a mass fraction of the mineral phase k in the HMSWtbt under initial conditions, $m_0$ is an initial sample mass of the HMSWtbt, $m_i$ is a mass of the dissociated solid residue after dissociation at the i-th concentration gradient, and $W_{ik}$ is the mass fraction of the mineral phase k in the dissociated solid residue after dissociation at the i-th concentration gradient;

S4, according to the formula $L_{n \times m} \times R_{m \times p} = Exp_{n \times p}$, solving an occurrence distribution proportion of the heavy metal element in the mineral phases expressed as $$R_{mxp} = \begin{pmatrix} r_{11} & \cdots & r_{1p} \\ \vdots & r_{kj} & \vdots \\ r_{m1} & \cdots & r_{mp} \end{pmatrix}, r_{kj} \in (0, 1);$$

and

S5, accumulating the occurrence distribution proportions of the heavy metal element j in each mineral phase of m mineral phases, and arranging the m mineral phases according to accumulated occurrence distribution proportions from high to low, and determining a mineral phase whose cumulative occurrence proportion exceeding a preset cumulative threshold value to be the key mineral phases of the heavy metal element j;

wherein, in a step of dissociation in the acid solutions with the n concentration gradients under the same set of dissociation conditions, the HMSWtbt is non-specifically dissociated in the acid solutions with the n concentration gradients, and the content of the heavy metal element in a dissociated solution after dissociation is measured; wherein an acid solution is a mixed acid solution comprising nitric acid: hydrochloric acid in a mol ratio of 1:3; a dissociation liquid-solid ratio is 8-12 L:1 kg; temperature is 15-35° C.; a dissociation time is 1-2 h; and an outer field effect comprises ultrasonic waves with an ultrasonic frequency of 20 kHz-40 KHz; and a power of 200-500 W;

wherein the method further comprises enabling selection of industrial solid waste treatment and disposal technologies based on the determined key mineral phases of the heavy metal element in the industrial solid waste; and wherein before a step S1, the method comprises a step of pre-cleaning of the HMSWtbt, and pre-cleaning steps include: mixing a pre-cleaning agent with the HMSWtbt at a liquid-solid ratio of 10 L: 1 kg, oscillating horizontally for 1-2 hours at 15-35° C., centrifuging an obtained solution at 6000 rpm-10000 rpm for 3-10 min to obtain a cleaning solution and the HMSWtbt after pre-cleaning; measuring a content of heavy metal elements in the cleaning solution, and quantitatively analyzing the HMSWtbt after pre-cleaning for the mineral phase, wherein 0.1 mol/L ammonium acetate solution with a pH=7.0 is used as the pre-cleaning reagent.

2. The method according to claim 1, wherein a calculating formula of the $d_{ij}$ comprises, $$d_{ij} = \frac{c_{ij} V_{ij}}{\omega_{oj} m_0} \omega_{0j}$$

is a mass fraction of the heavy metal element j in the HMSWtbt under the initial conditions, $c_{ij}$ is a concentration of the heavy metal element j in the dissociated solution after dissociation at the i-th concentration gradient, and $V_{ij}$ is a volume of the dissociated solution after dissociation at the i-th concentration gradient.

3. The method according to claim 2, wherein before the step S2, the method also comprises the step of pre-cleaning the HMSWtbt; wherein a calculating formula of the $$\omega_{0j} \text{ is } \omega_{0j} = \frac{\omega'_j m_a - c'_j V}{m_b}, \omega'_j$$

is the mass fraction of the heavy metal element j in the HMSWtbt without pre-cleaning, $m_a$ is a mass of the HMSWtbt without pre-cleaning, $m_b$ is the mass of HMSWtbt after pre-cleaning, $c'_j$ is the concentration of the heavy metal element j in the cleaning solution of the HMSWtbt after pre-cleaning, V is a volume of the cleaning solution of the HMSWtbt after pre-cleaning.

4. The method according to claim 1, wherein a sample of the HMSWtbt is air-dried at 60-105° C. and ground to a sample powder with a size below 200 meshes before mixing with the precleaning agent.

5. The method according to claim 1, wherein a number of n is equal to a number of mineral phases m of the HMSWtbt, wherein a hydrogen ion concentration range of the acid solution in the n concentration gradients for dissociation is 0-12 mol/L.

6. The method according to claim 1, wherein steps of quantitative analysis of the mineral phases include: obtaining an X-ray diffraction pattern through X-ray diffraction analysis and determining relative contents of all mineral phases in the dissociated solid residue based on a marked Rietveld full spectrum fitting and refining method, wherein a mineral phase not included in the dissociated solid residue is selected as an internal standard substance, which comprises alumina or zinc oxide.

7. The method according to claim 1, wherein the preset cumulative threshold value is 80%-95%.

8. The method according to claim 1, wherein the method for measuring the content of heavy metal elements is one or any combination of an inductively coupled plasma emission spectroscopy, an atomic absorption spectroscopy, an inductively coupled plasma mass spectrometry, and an atomic fluorescence spectroscopy.

* * * * *